United States Patent
Vignon et al.

(10) Patent No.: US 11,266,312 B2
(45) Date of Patent: Mar. 8, 2022

(54) SYSTEM AND METHOD FOR REAL-TIME CREATION OF CARDIAC ELECTRO-PHYSIOLOGY SIGNALS IN THE HEART

(71) Applicant: KONINKLIJKE PHILIPS N.V., Eindhoven (NL)

(72) Inventors: Francois Guy Gerard Marie Vignon, Andover, MA (US); Ameet Kumar Jain, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 257 days.

(21) Appl. No.: 16/343,101

(22) PCT Filed: Nov. 3, 2017

(86) PCT No.: PCT/EP2017/078255
§ 371 (c)(1),
(2) Date: Apr. 18, 2019

(87) PCT Pub. No.: WO2018/087016
PCT Pub. Date: May 17, 2018

(65) Prior Publication Data
US 2019/0313910 A1    Oct. 17, 2019

Related U.S. Application Data

(60) Provisional application No. 62/418,856, filed on Nov. 8, 2016.

(51) Int. Cl.
*A61B 5/00* (2006.01)
*A61B 90/00* (2016.01)
(Continued)

(52) U.S. Cl.
CPC ............ *A61B 5/0044* (2013.01); *A61B 5/066* (2013.01); *A61B 5/287* (2021.01); *A61B 5/6858* (2013.01);
(Continued)

(58) Field of Classification Search
CPC ....... A61B 5/0044; A61B 5/287; A61B 90/37; A61B 5/066; A61B 5/6858; A61B 8/12;
(Continued)

(56) References Cited

U.S. PATENT DOCUMENTS 6,556,695 B1    4/2003  Packer
7,477,763 B2 *  1/2009  Willis .................... A61B 5/287
                                              382/128
(Continued)

OTHER PUBLICATIONS

International Written Opinion, PCT/EP2017/078255, filed Jan. 30, 2018.

*Primary Examiner* — Joel Lamprecht

(57) ABSTRACT

An instrument for internal mapping includes a flexible elongated portion (702) and an expandable portion (710) coupled distally to the elongated portion, the expandable portion having one or more expandable loops. An array of sensors (706) and electrodes (708) is distributed on the expandable portion and is configured to concurrently register the instrument to real-time images of an anatomy using the sensors and measure electrical characteristics of the anatomy with the electrodes to generate an electro-physiology (EP) map having the anatomy and intensities of the electrical characteristics mapped together in the real-time images.

17 Claims, 7 Drawing Sheets

(51) Int. Cl.
*A61B 5/06* (2006.01)
*A61B 8/12* (2006.01)
*A61B 5/287* (2021.01)
*A61B 34/10* (2016.01)
*A61B 34/20* (2016.01)
*A61B 8/08* (2006.01)
*A61B 8/00* (2006.01)
*A61B 5/285* (2021.01)

(52) U.S. Cl.
CPC ............... *A61B 8/12* (2013.01); *A61B 90/37* (2016.02); *A61B 5/285* (2021.01); *A61B 8/0841* (2013.01); *A61B 8/0883* (2013.01); *A61B 8/4254* (2013.01); *A61B 2034/105* (2016.02); *A61B 2034/2051* (2016.02); *A61B 2034/2061* (2016.02); *A61B 2090/367* (2016.02); *A61B 2090/378* (2016.02); *A61B 2562/0209* (2013.01)

(58) Field of Classification Search
CPC .............. A61B 5/285; A61B 2034/105; A61B 2034/2051; A61B 2034/2061; A61B 2090/367; A61B 2090/378; A61B 8/0841; A61B 8/0883; A61B 8/4254; A61B 2562/0209; A61B 2034/2063
See application file for complete search history.

(56) References Cited

U.S. PATENT DOCUMENTS

| | | |
|---|---|---|
| 2003/0013958 A1 | 1/2003 | Govari |
| 2003/0093067 A1 | 5/2003 | Panescu |
| 2003/0231789 A1* | 12/2003 | Willis ..................... A61B 8/12 382/128 |
| 2007/0106146 A1 | 5/2007 | Altmann |
| 2014/0121470 A1 | 5/2014 | Scharf |
| 2014/0200457 A1 | 7/2014 | Shuros |

* cited by examiner

SYSTEM AND METHOD FOR REAL-TIME CREATION OF CARDIAC ELECTRO-PHYSIOLOGY SIGNALS IN THE HEART

CROSS-REFERENCE TO PRIOR APPLICATIONS

This application is the U.S. National Phase application under 35 U.S.C. § 371 of International Application No. PCT/EP2017/078255, filed on Nov. 3, 2017, which claims the benefit of U.S. Provisional Patent Application No. 62/418,856, filed on Nov. 8, 2016. These applications are hereby incorporated by reference herein.

BACKGROUND

Technical Field

This disclosure relates to electro-anatomical mapping, and more particularly to systems, devices and methods for mapping a heart using real-time electro-physiology signals.

Description of the Related Art

With the increase in longevity of cardiology patients, an increase in advanced cardiac disease, especially involving imbalances in cardiac electrical activity, may be observed. Cardiac electrophysiology (EP) interventions involve identifying areas of improper cardiac electrical activity, and then treating (usually by ablation) the identified areas. Mapping electrical pathways inside the heart chamber (e.g., left atrium) is performed prior to the intervention in many procedures. There is a need to be able to create realistic maps before, during and after the procedure to help increase the efficacy of the procedure.

Mapping systems can map the activity of a single point at a given moment of time. These "point by point" mapping systems are typically cumbersome, take time to operate (e.g., 20-60 minutes), suffer from cardiac motion, and have poor physiological/functional resolution. Multi-electrode, non-contact mapping systems do not work well due to lack of three-dimensional (3D) constraints.

SUMMARY

In accordance with the present principles, an instrument for internal mapping includes a flexible elongated portion and an expandable portion coupled distally to the elongated portion, the expandable portion having one or more expandable loops. An array of sensors and electrodes is distributed on the expandable portion and is configured to concurrently the instrument to real-time images of an anatomy using the sensors and measure electrical characteristics of the anatomy with the electrodes to generate an electro-physiology (EP) map having the anatomy and intensities of the electrical characteristics mapped together in the real-time images.

A system for internal mapping includes an instrument including a flexible elongated portion and an expandable portion coupled distally to the elongated portion, the expandable portion having one or more expandable loops and an array of sensors and electrodes distributed on the one or more expandable loops. An imaging system is configured to image an anatomy. A controller has an analysis module to receive the image data from the imaging system and electrical characteristic data from the electrodes to register the image data and the electrical characteristics data by employing the sensors to locate the instrument and to generate an electro-physiology (EP) map having imaged anatomy and intensities of the electrical characteristics mapped together in an image or images.

A method for electro-physiology (EP) mapping includes imaging an internal volume; registering an instrument to images of the internal volume using an array of sensors responsive to an external imaging system, the instrument including electrodes distributed on one or more expandable loops of the instrument, the electrode being located by the sensors; measuring electrical characteristics at the electrodes of the instrument; back-propagating measured electrical characteristics onto imaged geometry acquired of the internal volume during imaging; and concurrently displaying the measured electrical characteristics and the imaged geometry to generate an EP map.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
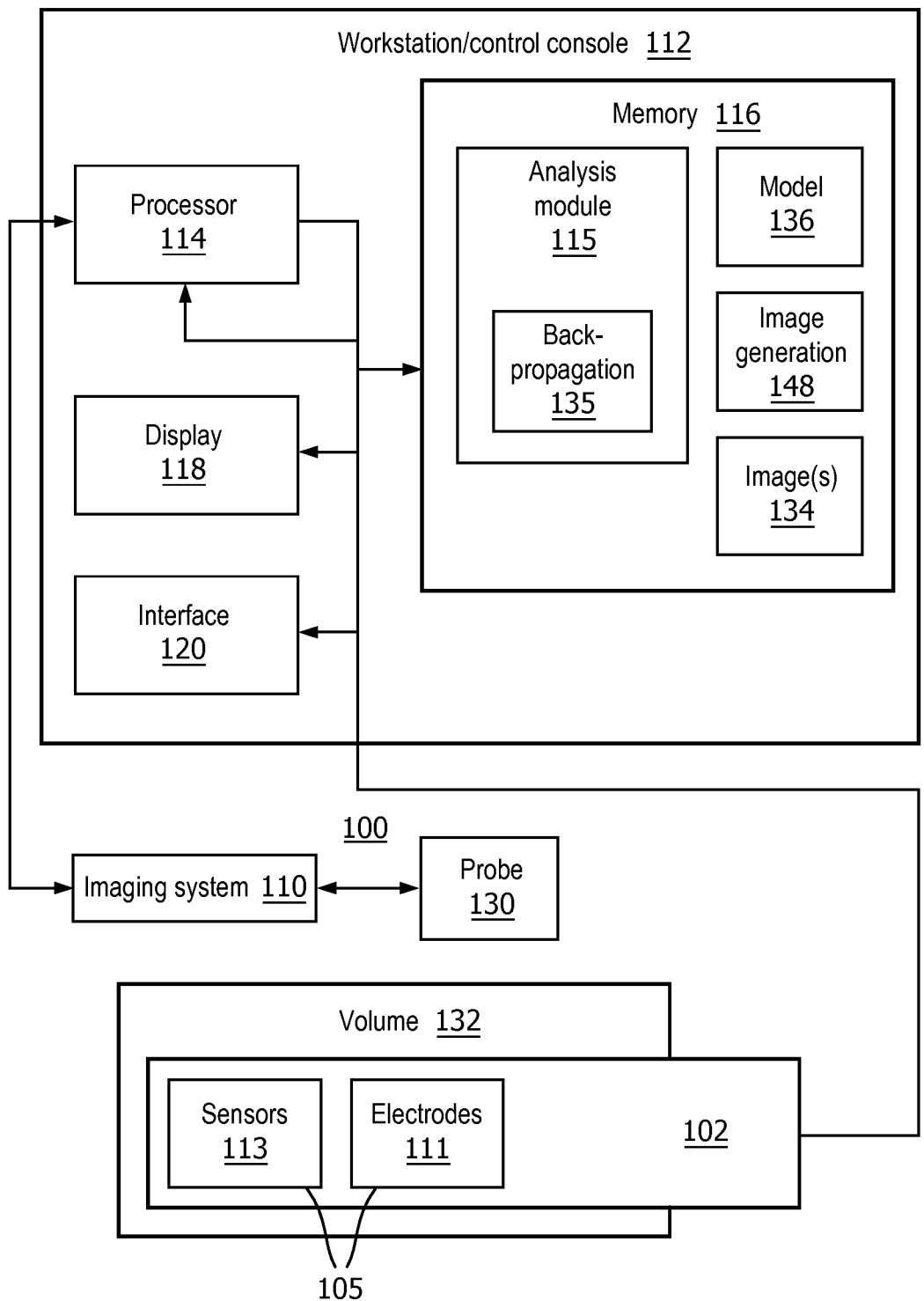
FIG. 1 is a block/flow diagram showing an electro-physiology mapping system, which employs an instrument having imaging sensors and electrodes for measuring electrical characteristics in accordance with one embodiment.

In accordance with the present embodiments, a live electro-anatomical mapping product and method for operation are provided. In one embodiment, an optional functional (mechanical) mapping is employed to complement electro-anatomical mapping. Current mapping products are limited in that an acquisition of the electrical maps is either cumbersome (required point-by-point contact of an electrode with the heart surface) or imprecise (e.g., non-contact electrical arrays rely on inaccurate assumptions to solve underdetermined inverse problems to reconstruct cardiac potentials from far-field potentials).

The present embodiments employ ultrasound imaging to obtain real-time anatomical information, and real-time tracking of a multi-electrode catheter or other instrument for precise registration of an electrode array and the anatomy. This permits precise reconstruction of cardiac potentials. In one embodiment, the electrode array is tracked with ultrasound (US) (which can include inSitu™ technology) with ultrasound sensors embedded in the electrode array. inSitu™ technology refers to one or more US receivers within a volume that can receive US signals from a US probe and compute a relative location based on time of flight, signal strength of other parameters. In addition to geometrical information for re-propagating activation potentials, ultrasound permits heart motion and deformation quantification. The present embodiments enable full three-dimensional (3D) characterization of electrical and mechanical parameters in a single module.

A challenge with inverse mapping catheters is that conventional catheters lack enough information to reconstruct complete and/or accurate information for a complete 3D map, at least to a level that is needed for clinical practice. The present embodiments employ real-time ultrasound (US) imaging for adding morphological information to assist in creating more accurate maps. The US could be two-dimensional (2D) or 3D, with 3D being preferred.

3D US information can be created using one or a plurality of matrix arrays or a tracked/navigated 2D US probe. Live ultrasound imaging can be employed in conjunction with heart modeling or registration to pre-operative computed tomography (CT), cone beam CT, magnetic resonance imaging (MRI), etc. to complement anatomical information. The 3D anatomical information during heart beating, and the concurrent raw voltages measured by the inverse mapping catheters, can be integrated together with a precise electromechanical model. To do so, the information is registered in a highly precise manner. In one embodiment, InSitu™ technology can be employed, which can register/track small piezo-sensitive sensors inside the US field of view with an accuracy of, e.g., about 0.25 mm—about 0.5 mm.

In alternate embodiments, different tracking technologies, such as electromagnetic (EM) or Fiber-Optical RealShape™ (FORS™, also known as Optical Shape Sensing (OSS), Fiber Shape Sensing, Fiber Optical 3D Shape Sensing, Fiber Optic Shape Sensing and Localization or the like) can be employed. A Fiber-Optical RealShape™ or FORS™ is a commercial name for systems developed by Koninklijke Philips, N.V. As used herein, the terms FORS™ and FORS™ systems are not, however, limited to products and systems of Koninklijke Philips, N.V., but refer generally to fiber optic(al) shape sensing and fiber optic(al) shape sensing systems, fiber optic(al) 3D shape sensing, fiber optic(al) 3D shape sensing systems, fiber optic(al) shape sensing and localization and similar technologies. FORS systems are also commonly known as "optical shape sensing systems".

It should be understood that the present invention will be described in terms of medical instruments; however, the teachings of the present invention are much broader and are applicable to any instruments or systems that employ internal mapping. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, excretory organs, blood vessels, etc. and especially the heart. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 that combines US (3D) and electrical measurements for live, dense, accurate electro-anatomic maps (EAMs) is illustratively shown in accordance with one embodiment. System 100 can include a workstation or control console 112 from which a procedure is supervised and/or managed. Workstation or control console 112 is responsible for interfacing between instrument, imaging, and registration systems. Workstation 112 preferably includes one or more processors 114 and memory 116 for storing programs and applications. Memory 116 stores analysis tools and registration tools for processing US signals and models. Memory 116 also stores other tools, operating systems and programs or functions needed for the control console 112 and its peripherals.

An analysis module 115 is configured to interpret and/or register US images collected using an imaging system 110 (preferably an ultrasound system, although other imaging systems may be employed) with one or more models or preoperative images taken on an anatomical feature or volume 132 (e.g., the heart). The analysis module 115 runs programs for registration of data/images, to perform back-propagation of electrical fields, and to provide electro-mechanical analysis or other analysis. The back-propagation of electric fields includes a program or algorithm that associates measured electric fields with an anatomical structure or surface. In this way, the measured electrical properties, e.g., dipole density, voltage, etc., can be mapped on or with the anatomical structure so that a determination can be made as to the tissues status. For example, in an ablation process, the characteristics of ablated material will be different from unablated material. This leads to a better understanding of the progress of the ablation while more accurately preserving healthy tissue.

The US imaging system 110 enables live 2D or 3D acquisition of anatomy and motion of the feature 132 (e.g., the heart). The US imaging system 110 preferably acquires views from a transthoracic perspective. In one embodiment, the 3D anatomy can be achieved by stitching 2D views from an ultrasound probe 130. In some embodiments, the ultrasound probe 130 can be transesophageal echocardiography (TEE) or intracardiac echocardiography (ICE) probe.

A medical device or instrument 102 can include a catheter, a guidewire, a probe, an endoscope, a robot, an electrode, a filter device, a balloon device, or other medical component. The instrument 102 preferably includes an intracardiac instrument on a catheter having an array 105 of electrodes 111 and/or sensors 113 for US mapping and electrical mapping of a heart.

The instrument 102 may include sensors/devices 113 for other technologies for internal mapping, e.g., one or more optical fibers for FORS™ shape sensing, EM sensors, etc., which may be coupled to the instrument 102 in a set pattern or patterns. The sensors/devices 113 connect to the workstation 112 through the instrument 102, as needed. In one embodiment, the instrument 102 includes the intracardiac array 105 with electrodes 111 for acquisition of electrical signals inside the heart using a non-contact electrodes (e.g., the electrodes that make measurements that do not touch the myocardium). The array 105 includes sensors 113 co-located with the electrodes 111 for registration with ultrasound images from the US imaging system 110. In a particularly useful embodiment, the sensors 113 include ultrasound receivers (e.g., lead zirconate titanate (PAT), polyvinylidene fluoride (PVDF), copolymer, fiber-optic-based receivers, etc.) that indicate a position and orientation (tracking function) of the instrument and therefore the electrodes at a given time. The instrument 102 includes a tracking technology for the tracking function, such as an ultrasound-based (inSitu™) tracking technology using the ultrasound imaging system 110.

The electrodes 111 make measurements of electrical characteristics. These measurements are back-propagated to associate the electrical characteristics with anatomical geometry. The back-propagation in performed by a back-propagation module 135. The back-propagation module 135 employs known relationships between anatomical features and measured electrical characteristics to more accurately determine voltages, charge, dipole density, etc. on a surface or image of the volume 132 (e.g., the heart).

In one embodiment, workstation 112 includes an image generation module 148, which is configured to receive feedback from the array 105 and register the feedback with images, models or other data. The image generation module 148 renders one or more sets of data for concurrent display and further manual manipulation. An image or images 134 of the internal volume or feature 132 can be displayed on a display device 118. Workstation 112 includes the display 118 for viewing internal images of the volume 132 and may include the image 134 as an overlay(s) or other rendering, as needed. The display 118 can output surface cardiac potentials, mechanical information, and the relationship between these.

Mechanical information (e.g., deformation information) and other mechanical properties may be determined from the imaging system 110 (US). The mechanical information may be displayed concurrently with the electrical characteristic data and/or the images 134. A model or models 136 can be stored in the memory 116. In one embodiment, the model 136 includes a dynamic heart model that simulates motion of the heart (or other organ) to assist in accurately accounting for heart motion in images. This assists in registration of the instrument 102, registration between preoperative images and real-time images and mapping electrical characteristics to a beating heart.

The display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

In a particularly useful embodiment, the catheter 102 includes a plurality of electrodes 111 to acquire electrical signals in a non-contact manner. The positions of the electrodes 111 are registered with the external imaging system 110 (preferably ultrasound) with tracking technology (preferably inSitu™). The external imaging system 110 may optionally include heart model fitting or registration to pre-op imaging and provides anatomical image information. The external imaging system 110 can also provide mechanical information. Real-time measured positions of the electrodes, together with the real-time measured position of the heart anatomy, permit re-propagation of the electrical signals acquired by the electrodes 111 onto the surface of the heart (132) or other structure to provide accurate electrical maps. The electrical maps are displayed on the display 118 together with mechanical activation maps.

Figure 2:
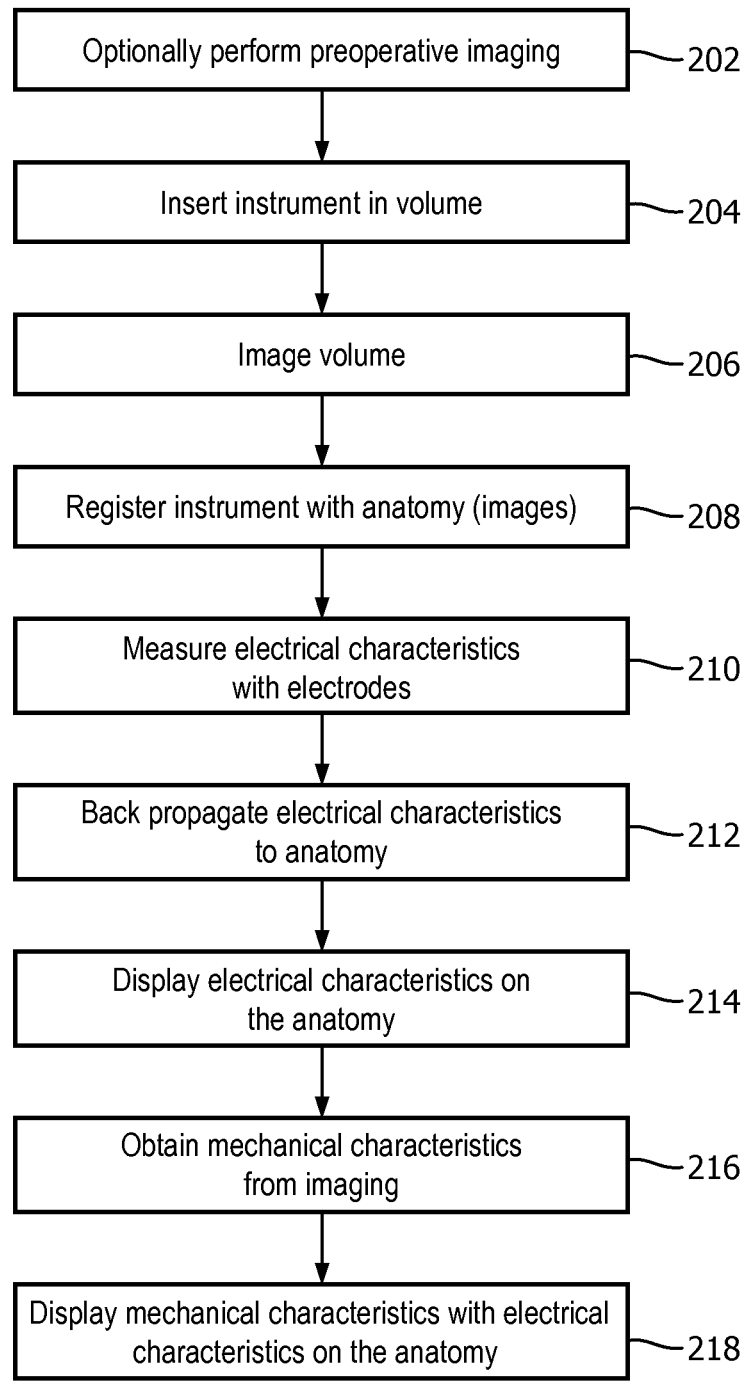
FIG. 2 is a flow diagram showing methods for electro-physiological mapping, which concurrently displays electrical characteristics on images in accordance with one embodiment.

Referring to FIG. 2, methods for electro-anatomical mapping a heart or other organ are shown in accordance with illustrative embodiments. It should be understood that the blocks set forth in FIG. 2 may be taken in any order and that steps outlined herein may be conducted concurrently and in real-time. For example, electrical measurements and imaging can be conducted concurrently.

In block 202, pre-operative imaging may optionally be performed. This may include MRI, CT, US, etc. The images may be employed to improve image accuracy by registering the preoperative images with real-time images. In block 204, an instrument is inserted into an internal volume, e.g., a heart chamber or other internal volume. The instrument may include a flexible elongated portion (e.g., a catheter, etc.). An expandable portion may be coupled distally to the elongated portion. The expandable portion includes one or more expandable loops and may include a basket catheter or the like. An array of sensors and electrodes are distributed on the expandable portion.

In block 206, the heart chamber or other volume is imaged with US (e.g., 3D or 2D US). This includes real-time imaging. The external imaging system (preferably ultrasound, optionally with heart model fitting or registration to pre-op imaging) provides anatomical information, and can optionally provide mechanical information about the heart (or other organ). In block 208, the instrument is registered with anatomy on the US images. Any suitable registration method may be employed. The position of the electrodes is registered with an external imaging system (preferably US) with tracking technology (preferably inSitu™, which uses the US sensors as beacons to indicate their position to the external imaging system). In one embodiment, the external US imaging system sends US signals, which are received by US sensors. The US sensors reveal their location using the time of flight, signal strength and other US characteristics. The position of the instrument and therefore the electrode is obtained and can be registered with the anatomical images.

In block 210, electrical characteristics (e.g., voltages, charges, dipoles densities, etc.) are measured at electrodes of the electrode array of the instrument. In block 212, the measured electrical characteristics, information on anatomy and electrode locations (e.g., results of blocks 206-210) are combined to back-propagate an association of the electrical characteristics to anatomical features in the volume. The real-time measured positions of the electrodes (block 208), together with the real-time measured position of the heart anatomy (block 206), permit re-propagation of the electrical signals acquired by the electrodes (block 210) onto the heart surface to provide accurate electrical maps. For example, voltages are back-propagated to a heart surface to obtain cardiac voltages, charges and dipole density in regions of the heart. Back-propagating the measured voltages onto the accurate geometry acquired in block 204 makes the back-propagation more accurate than assuming a given geometry (as in conventional techniques). The motion of the heart may be computed in a model and the motion of the model can be correlated to the electrical measurements and the image of the heart beating. The measured electrical response can be predicted using the model so that a correlation between the heart motion and the electrical responses can be aligned.

In block 214, a spatio-temporal distribution of cardiac electrical characteristics (e.g., voltages) obtained in block 212 are displayed on a display device on the imaged anatomy. In block 216, mechanical characteristics, e.g., deformation information from US imaging may optionally be obtained. In block 218, the spatio-temporal information on electrical activation (from block 212) and the mechanical deformation (from block 216) are combined into a same display generation module and displayed concurrently. The electrical maps can be displayed together with mechanical activation maps.

Figure 3:
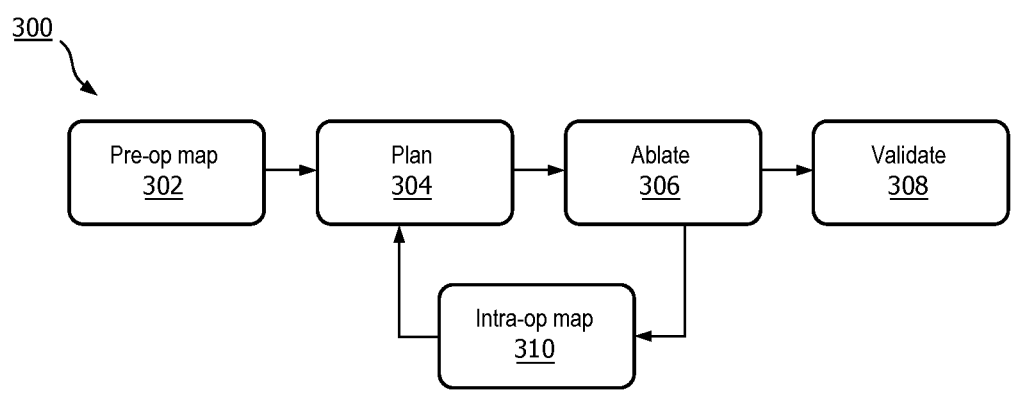
FIG. 3 is a flow diagram showing an illustrative workflow where electro-physiological mapping is employed as feedback in accordance with one embodiment.

Referring to FIG. 3, in accordance with one embodiment, a workflow 300 for electro-physiology (EP) is updated using an intra-operative feedback loop 310 for updating an operative plan 304. In one example, the operative workflow 300 may include a heart ablation procedure. Beginning with preoperative images (e.g., MRI, CT, US, X-ray, etc.), a preoperative map 302 of the heart (or other organ) can be created. Using the pre-operative map 302, the plan 304 is formulated. The plan identifies the parts of the heart that will be treated and how they will be treated, e.g., ablation parameters, etc. In block 306, ablation is performed in accordance with the plan 304.

However, in accordance with the present principles the plan is updated using the feedback loop 310. The feedback loop 310 includes the use of EP map updates generated through the methods described with respect to FIG. 2. The feedback provides highly accurate new information on the heart and can be employed to adjust the plan in real-time. After ablation, the results are validated in validation block 308. Because of the real-time mapping capability, the feedback loop 310 can improve results for all EP labs and EP interventions before, during and after the procedure and can be used to update the ablation plan 304 during the ablation 306. The mapping system in accordance with the present embodiments can create EAM maps faster, and with greater precision than conventional systems.

Figure 4:
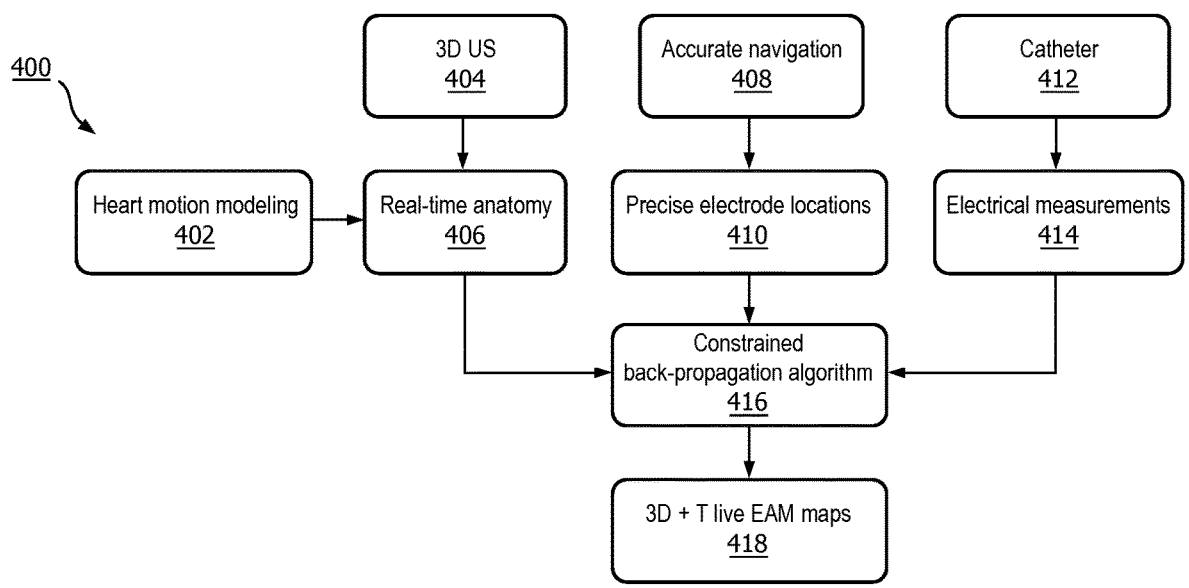
FIG. 4 is a block/flow diagram showing an electro-physiology mapping system and processing flow which employs an instrument having imaging sensors for locating an instrument in a volume and electrodes for measuring electrical characteristics which are back propagated and displayed together in a map in accordance with one embodiment.

Referring to FIG. 4, the mapping system in accordance with the present embodiments can employ a plurality of data sources to increase the accuracy. These different data sources can include models, images, navigation data, electrical measurements etc. employed in generating a real-time map update. A block diagram 400 illustratively shows the interaction between data sources in generating spatial-temporal (3D+T) EAM maps 418 in real-time. A heart model 402 can be employed and, in particular, a model representing the motion of a beating heart. The model 402 can be used in conjunction with real-time anatomical images 406, which can be gathered using a real-time imaging system 404, such as, a 2D or 3D ultrasound imaging system. The model 402 and the images 404 can be registered or otherwise combined to understand and predict the motion of the heart.

More specifically, the model 402 is either a statistical model derived from a patient population, or a tailored model made to represent the particular patient. In the latter case, the model 402 can be derived from segmentation of CT or cone-beam CT pre-operative images. The temporal dynamics of the heart may or may not be included in the model 402. Under ultrasound imaging, the model 402 is dynamically fitted to a live ultrasound view to enhance the viewing experience, displaying the heart boundaries in an intuitive way. The model 402 is also employed to extrapolate the heart position beyond the parts that are visible under ultrasound's limited field of view. The model 402 can be an existing model enhanced in accordance with the present principles.

Accurate secondary navigation systems 408 can be employed to define a relative position between an EP instrument, e.g., a catheter 412 or other device having electrodes and/or sensors disposed thereon. The accurate navigation systems 408 may include EM, FORS™, US responsive sensors, or any other suitable navigation system. The accurate navigation system 408 is employed to determine the positions of the electrodes and/or sensors of the instrument when disposed internally to map the heart. The catheter 412 employs the electrodes and/or sensors to make electrical measurements of the beating heart. These measurements are preferably performed inductively or capacitively without making contact with the heart.

The data collected including the real-time anatomy 406, electrical measurements 414 and electrode positions 410 are used as inputs to a constrained back-propagation algorithm 416. The constrained back-propagation algorithm 416 can include a method that associates the electrical measurements with positions on the heart. The constrained back-propagation algorithm 416 uses the electrode positions 410, the position of the heart (406) and the electrical measurements 414 to associate and place the electrically measured parameters at positions on the heart. This, in turn, generates the live EAM maps 418. The maps 418 are generated in real-time and therefore are frequently updated so that the map provides visual guidance in the form of a map showing the electrical properties associated with the positions of the heart. This provides information showing the health of the tissue, regions that have been ablated, regions to be ablated in accordance with the plan and feedback for updating the plan in order to achieve the goals of the plan.

Figure 5:
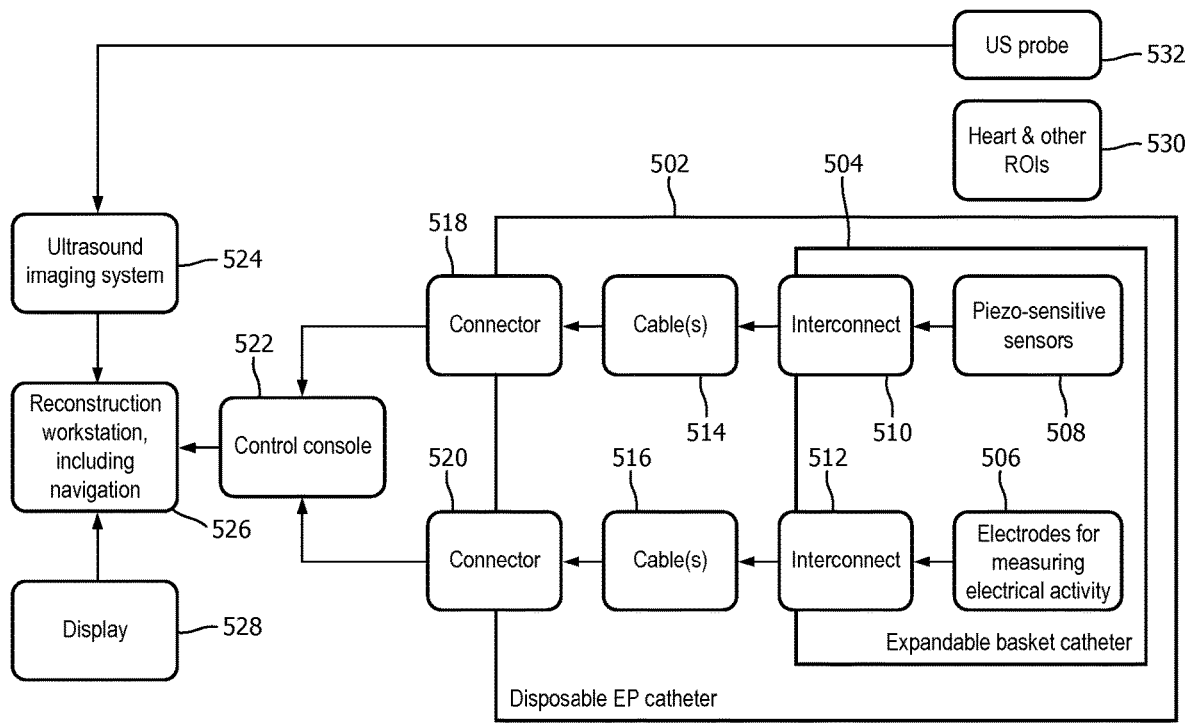
FIG. 5 is a block/flow diagram showing an instrument employed for an electro-physiology mapping system in greater detail and showing processing flow which employs the instrument to display images of the volume and measured electrical characteristics together in a map in accordance with one embodiment.

Referring to FIG. 5, a block/flow diagram shows an instrument 502 (see also instrument 102 in FIG. 1) and hardware connections between components in greater detail. In a particularly useful embodiment, the instrument 502 includes an expandable basket catheter 504, which can include a mechanism for expanding and/or contracting a configuration for a portion of the catheter. In one embodiment, a non-contact mapping expandable catheter 504 may include an expansion cage or a balloon. The expandable catheter 504 includes ultrasound transducers or sensors 508 arranged on the catheter 504 for locating positions of electrodes 506 inside a heart or other regions of interest (ROI) 530 using an US probe 532 of an US imaging system 524. Live anatomy (and function) is obtained from the US imaging system 524. The ultrasound transducers or sensors 508 can be arranged in a simple array or may include a complex arrangement on the expandable catheter 504. The sensors 508 are responsive to the US signals and reveal their positions to a control console 522 through signals on cable(s) 514. The expandable catheter 504 can also include an array of electrodes for measuring electrical activity of the heart or other ROI 530.

The expandable catheter 504 includes interconnects 510 and 512 employed for making electrical connections to the sensors 508 and electrodes 506, respectively. The expandable catheter 504 connects to or is assembled with the instrument 502, which can include a disposable EP catheter or the like. The instrument 502 may include cables 514 and 516 that connect to interconnects 510, 512. The cables 514, 516 may, in turn, connect with the control console 522. The control console 522 and a reconstruction workstation 526 may be part of a single computer console (e.g., workstation 112 in FIG. 1) or be separate components. The reconstruction workstation 526 includes the back-propagation algorithm and hosts programs for navigation systems. A display 528 is employed to render the EAM maps for real-time updating of the heart or ROI 530 images that can provide still images or video of the beating heart showing electrical characteristics (e.g., dipole density, voltages, etc.) along with mechanical (e.g., displacement, velocity, acceleration, strain, strain rate, etc.) and visual characteristics of the heart or ROI 530.

Figure 6:
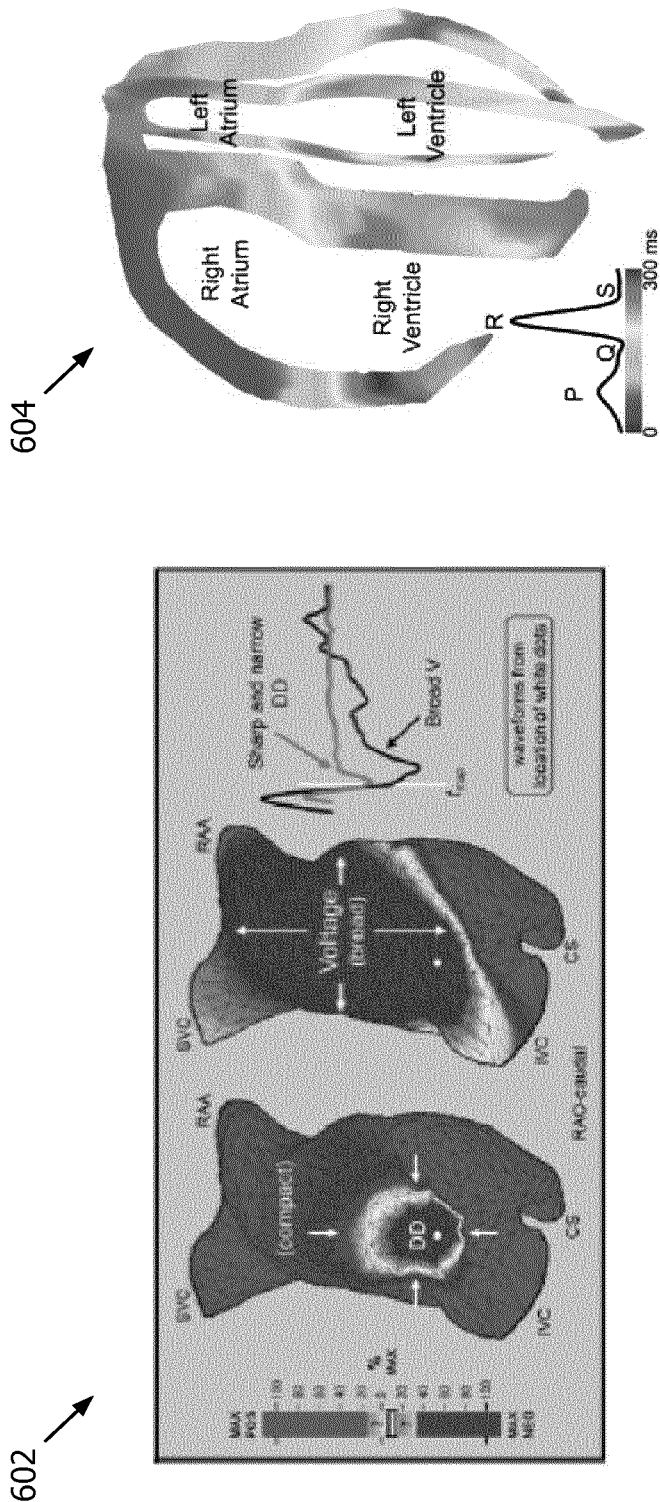
FIG. 6 shows one image of a heart having electrical characteristics mapped and another image of a heart having mechanical characteristics mapped in accordance with one embodiment.

Referring to FIG. 6, electrical activation maps (EAM) 602 can include intensity maps integrated with anatomical maps and/or mechanical activation maps 604. These can be obtained from the anaysis of ultrasound data from the ultrasound system and electrode measurements employed in accordance with the present embodiments. The color scales of these maps can be configured to indicate times of onset of electrical and mechanical activations, repectively. These maps 602 and 604 are displayed concurrently on a same anatomical image or model, which is of interest to a clinician both for planning and monitoring a procedure.

Figure 7:
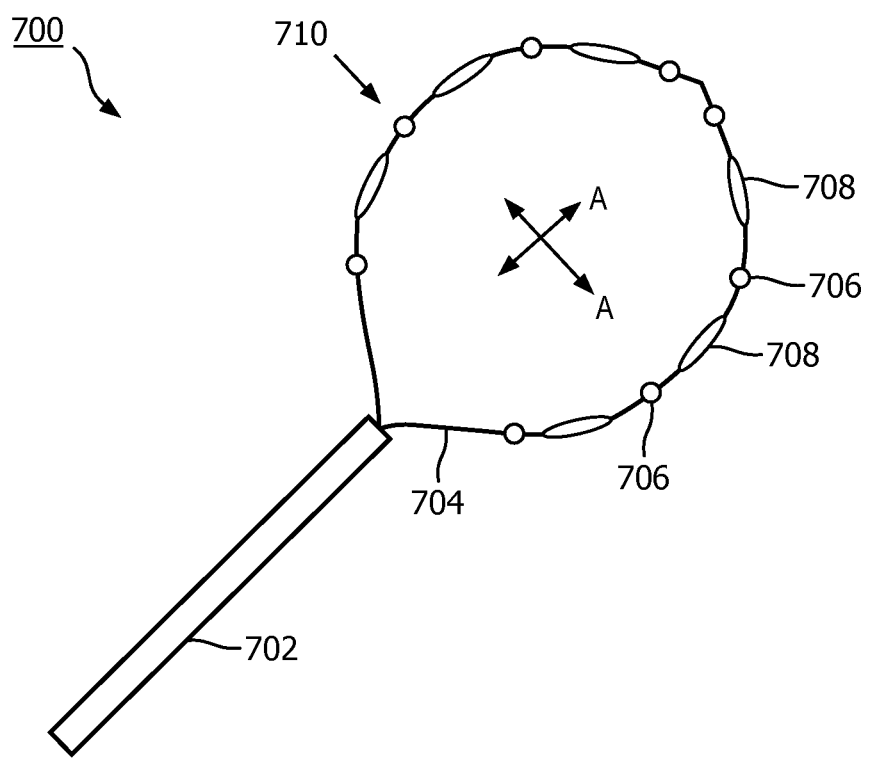
FIG. 7 is a side view of a distal end portion of an instrument having sensors and electrodes distributed on an extendable loop in accordance with one embodiment.

Referring to FIG. 7, an instrument 700 includes an expandable portion 710 (e.g., a basket), which can include one or more expandable loops 704 for expanding and/or contracting a configuration on a catheter 702. In one embodiment, the expandable portion 710 includes electrodes 708 and sensors (e.g., US) 706 disposed in an array along the loop 704. The loop 704 includes a flexible or semi-rigid structure that can have a lumen for carrying electrical wires (not shown) back through the catheter 702. The lumen can also permit a FORS™ or other navigation system sensor to be deployed. In one embodiment, the loop 704 may carry an EM sensor.

The portion 710 may include a plurality of loops 704 that can form a cage or basket. The loop or loops can expand (or contract) as indicated by arrows "A". The sensors 706 of the catheter portion 710 can include ultrasound transducers arranged on the loop 704 to get live cardiac anatomy from inside a heart or other regions of interest (ROI). The electrodes 708 are configured in an array to take dipole densities or voltage measurements (among other parameters) of the heart.

Instrument 700 concurrently locates electrodes form registration to real-time images and at the same time provides electrical characteristics for the real-time imaged locations. By employing the instrument 700 in a procedure, fast and accurate feedback can be provided for visual display in real-time.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for real-time creation of cardiac electro-physiology signals in the heart (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for internal mapping, comprising:

an instrument including a flexible elongated portion and an expandable portion coupled distally to the elongated portion, the expandable portion having one or more expandable loops and an array of sensors and electrodes distributed on the one or more expandable loops, the sensors configured to generate position data of the electrodes within an anatomy, the electrodes configured to generate electrical characteristics data of the anatomy;

an external imaging system configured to generate image data of the anatomy and send signals to the sensors; and a controller having an analysis module to concurrently receive the image data from the external imaging system, the position data from the sensors, and the electrical characteristic data from the electrodes, as well as generate images from the image data, the controller configured to:

register position of the instrument, computed using time of flight and signal strength of the signals sent by the external imaging system, to images of the image data of the anatomy based on the position data, back-propagate the electrical characteristics data to associate parameters of the electrical characteristic data with positions on the anatomy in the images based on (i) the position data and (ii) predetermined relationships between anatomical features of the anatomy and the electrical characteristics data, and generate in real-time an electro-anatomical map including the back-propagated electrical characteristics data displayed on the images of the anatomy.

2. The system as recited in claim 1, wherein the electro-anatomical map further includes mechanical data of the anatomy displayed on the images of the anatomy.

3. The system as recited in claim 1, wherein the parameters of the electrical characteristics data include one or more of voltage, charge and/or dipole density.

4. The system as recited in claim 1, further comprising a secondary navigation system configured to track the instrument within the anatomy.

5. The system as recited in claim 1, wherein the external imaging system includes an ultrasound system and the sensors include ultrasound sensors to determine a position of the instrument and the electrodes.

6. The system as recited in claim 1, wherein the controller includes a back propagation program that associates the parameters comprising measured electrical characteristics of the anatomy derived from the electrical characteristic data with a structure or a surface of the anatomy derived from the image data.

7. The system as recited in claim 1, further comprising a display to display the electro-anatomical map to provide real-time feedback of anatomical changes as measured by the electrical characteristics data and the image data.

8. A method for electro-anatomical mapping of an internal volume, the method comprising:

imaging, by an external imaging system, the internal volume having an instrument therein to generate images of the internal volume, the instrument including an array of electrodes and sensors distributed on one or more expandable loops of the instrument, the electrodes being locatable by the sensors and the sensors being configured to receive signals sent by the external imaging system and generate position data of the electrodes within the internal volume;

registering, by a controller, the instrument to the images of the internal volume using time of flight and signal strength of the signals sent by the external imaging system;

measuring, by the controller, electrical characteristics of the internal volume at the electrodes of the instrument;

back-propagating, by the controller, the measured electrical characteristics to associate parameters of the measured electrical characteristics with positions of an anatomy in the imaging of the internal volume by the external system based on (i) the position data and (ii) predetermined relationships between anatomical features of the anatomy and the measured electrical characteristics;

generating in-real time, by the controller, an electro-anatomical map including the back-propagated measured electrical characteristics of the interval volume displayed on images of the imaging of the internal volume by the external imaging system; and displaying, by a display, the electro-anatomical map.

9. The method as recited in claim 8, wherein measuring, by the controller, of the electrical characteristics of the internal volume includes measuring the electrical characteristics of the internal volume with non-contact electrodes.

10. The method as recited in claim 8, wherein the displaying, by the display, of the electro-anatomical map includes displaying a real-time three-dimensional image of the internal volume with the electrical characteristics as feedback for a procedure.

11. The method as recited in claim 8, wherein the back-propagating, by the controller, of the measured electrical characteristics of the internal volume includes an accounting, by the controller, for motion of the internal volume using a dynamic model which models the motion.

12. The method as recited in claim 8, further comprising obtaining, by the controller, mechanical deformation information of the internal volume from the imaging of the internal volume by the external imaging system; and concurrently displaying, by the display, the mechanical deformation information and the electro-anatomical map.

13. A non-transitory computer-readable storage medium having stored a computer program comprising instructions, the instructions, when the computer program is executed by a processor, cause the processor to:

receive an image, from an external imaging system, the internal volume having an instrument therein to generate images of the internal volume, the instrument including an array of electrodes and sensors distributed on one or more expandable loops of the instrument, the electrodes being locatable by the sensors and the sensors being configured to receive signals sent by the external imaging system and generate position data of the electrodes within the internal volume;

register the instrument to the images of the internal volume using time of flight and signal strength of the signals sent by the external imaging system;

measure electrical characteristics of the internal volume at the electrodes of the instrument;

back-propagate the measured electrical characteristics to associate parameters of the measured electrical characteristics with positions of an anatomy in the imaging of the internal volume by the external system based on (i) the position data and (ii) predetermined relationships between anatomical features of the anatomy and the measured electrical characteristics;

generate, in-real time, an electro-anatomical map including the back-propagated measured electrical characteristics of the interval volume displayed on images of the imaging of the internal volume by the external imaging system; and cause display of the electro-anatomical map.

14. The storage medium as recited in claim 13, wherein measurement, by the processor, of the electrical characteristics of the internal volume includes measurement of the electrical characteristics of the internal volume with non-contact electrodes.

15. The storage medium as recited in claim 13, wherein display, by the processor, of the electro-anatomical map includes display of a real-time three-dimensional image of the internal volume with the electrical characteristics as feedback for a procedure.

16. The storage medium as recited in claim 13, wherein back-propagation, by the processor, of the measured electrical characteristics of the internal volume includes an accounting for motion of the internal volume using a dynamic model which models the motion.

17. The storage medium as recited in claim 13, wherein the instructions, when the computer program is executed by the processor, further cause the processor to obtain mechanical deformation information of the internal volume from the imaging of the internal volume by the external imaging system; and concurrently displaying, by the display, the mechanical deformation information and the electro-anatomical map.

* * * * *